United States Patent
Jones, III

(10) Patent No.: US 6,225,356 B1
(45) Date of Patent: May 1, 2001

(54) CROMOLYN SODIUM CONTAINING COMPOSITION AND METHOD OF TREATMENT FOR VILVAR VESTIBULITIS INTERSTITIAL CYSTITIS VUKVAR VAGINITIS AND VAGINITIS DYNEA

(76) Inventor: Tudor Jones, III, 8745 Hampshire Glen Dr., Jacksonville, FL (US) 32256

( * ) Notice: Subject to any disclaimer, the term of this patent is extended or adjusted under 35 U.S.C. 154(b) by 0 days.

(21) Appl. No.: 09/488,317

(22) Filed: Jan. 20, 2000

(51) Int. Cl.$^7$ .................................................. A61K 43/30
(52) U.S. Cl. ...................... 514/772.3; 514/941; 514/944; 514/969; 514/789; 514/887; 424/400; 424/433
(58) Field of Search ................................. 514/54, 78, 941, 514/944, 969, 789, 887; 424/400, 433

(56) References Cited

U.S. PATENT DOCUMENTS 5,817,699 * 10/1998 Flores et al. ........................ 514/647
6,083,933 * 7/2000 Hahn ..................................... 514/54

FOREIGN PATENT DOCUMENTS

WO 99/00130 * 1/1999 (WO) .

* cited by examiner

*Primary Examiner*—Thurman K. Page
*Assistant Examiner*—Liliana Di Nola-Baron
(74) *Attorney, Agent, or Firm*—Thomas C. Saitta

(57) ABSTRACT

A composition and method for the treatment of the conditions vulvar vestibulitis, interstitial cystitis, vulvar vaginitis or vaginitis dynea wherein a composition containing cromolyn sodium in effective amount is applied to the vaginal vestibule area, with the application repeated as necessary to effectively address the symptoms and conditions. Preferably, the cromolyn sodium is present in an amount of about 2 to 10 percent in a carrier ointment or cream, with the carrier composition preferably comprising a mixture of pluronic gel and lecithin organogel.

6 Claims, No Drawings

CROMOLYN SODIUM CONTAINING COMPOSITION AND METHOD OF TREATMENT FOR VILVAR VESTIBULITIS INTERSTITIAL CYSTITIS VUKVAR VAGINITIS AND VAGINITIS DYNEA

BACKGROUND OF THE INVENTION

This invention relates most generally to the field of therapeutic topical ointments containing cromolyn sodium and to therapeutic treatments for the pain and discomfort of such conditions as vulvar vestibulitis, interstitial cystitis, vulvar vaginitis or vaginitis dynea.

Vulvar vestibulitis, interstitial cystitis, vulvar vaginitis and vaginitis dynea are relatively common conditions of the female vaginal, vulvar, and urinary areas, causing discomfort or pain during sexual intercourse or urination, or an increase in the frequency of urination. The conditions are believed to result from inflammation of specific areas. Typical anti-inflammatory treatments have proven ineffective against these conditions. Ineffective treatments for vulvar vestibulitis, which is localized in the vestibule area comprising the meeting point of the vulva and the vagina and which contains the Bartholin's glands, the urethra and minor vestibular glands, include steroid, zinc oxide and ketoconazole creams, as well as oatmeal sitz baths, calendula and hypercal creams, bland aqueous creams and the application of tea bags. Interstitial cystitis is a chronic inflammatory condition of the bladder wall and is not related to common cystitis, which is a urinary tract infection caused by bacteria. Interstitial cystitis is not caused by bacteria and does not respond to antibiotic therapy. Ineffective treatments include oral medications such as pentosan polysulfate sodium, tricyclic antidepressants, antispasmodics, antihistamines and muscle relaxants, as well as bladder distention and injection of dimethyl sulfoxide, heparin, silver nitrate, oxychlorosene sodium, bacillus Calmette-Guerin or hyaluronic acid.

Cromolyn sodium is a known therapeutic composition which inhibits the degranulation of sensitized mast cells which occurs after exposure to specific antigens. The cromolyn inhibits the release of histamine and SRS-A (slow-reacting substance of anaphylaxis) from the mast cell. Some studies have shown that cromolyn further inhibits the degranulation of non-sensitized mast cells by phospholipase A and the subsequent release of chemical mediators, although contrary studies exist. Cromolyn has no intrinsic vasoconstrictor, antihistaminic or anti-inflammatory activity. Cromolyn sodium is well known in the treatment of certain conditions of the eye, such as vernal keratoconjunctivitis, vernal conjunctivitis and vernal keratitis, as well as in the treatment of certain allergic reactions and contact blepharitis. Cromolyn sodium is also used in the treatment of certain heart conditions, asthma, gastrointestinal conditions and skin conditions such as eczema or psoriasis. Cromolyn sodium has not been used in the treatment of vulvar vestibulitis, interstitial cystitis, vulvar vaginitis or vaginitis dynea.

It is an object of this invention to provide a novel method and composition for topical application which effectively treats the conditions of vulvar vestibulitis, interstitial cystitis, vulvar vaginitis and vaginitis dynea, where the active ingredient cromolyn sodium is provided in a therapeutically effective amount via a carrier composition or ointment.

SUMMARY OF THE INVENTION

The invention comprises a composition and method for the treatment of the conditions vulvar vestibulitis, interstitial cystitis, vulvar vaginitis or vaginitis dynea wherein a composition containing cromolyn sodium in effective amount is applied to the vaginal vestibule area, with the application repeated as necessary to effectively address the symptoms and conditions. Preferably, the cromolyn sodium is present in an amount of about 2 to 10 percent in a carrier ointment or cream, with the carrier composition preferably comprising a mixture of pluronic gel and lecithin organogel.

DETAILED DESCRIPTION OF THE INVENTION

In general, the invention comprises a composition and a method for the therapeutic treatment of painful and discomforting conditions resident in the female vaginal and urinary area, such as vulvar vestibulitis, interstitial cystitis, vulvar vaginitis or vaginitis dynea through the topical application of cromolyn sodium present in therapeutically effective amount in a carrier composition. The method of treatment comprises a single or repeated topical application to the vaginal, vulvar, urinary or vestibule region of the composition as fully described below until the symptoms or conditions are significantly reduced or obviated. Preferably, the composition is applied approximately 3 to 4 times daily for a period of at least 3 to 4 days. While cromolyn sodium is a known therapeutic composition for the treatment of certain conditions, it is not heretofore known to be useful or efficacious in the treatment of vulvar vestibulitis, interstitial cystitis, vulvar vaginitis or vaginitis dynea, or any related conditions.

The composition comprises cromolyn sodium is a carrier cream or ointment composition. Cromolyn sodium is represented by the chemical formula $C_{23}H_{14}Na_2O_{11}$ with the chemical name of disodium 5,5'-[(2-hydroxytrimethylene) dioxyl[bis]4-oxo-4H-1-benzopyran-2-carboxylate]. Cromolyn sodium is sold by various manufacturers under the trade names SODIUM CROMOLYN, LOMUDAL, NASMIL and AARANE. It is a registered prescription item with National Drug Code (NDC) no. 51552-0423-99.

The composition preferably comprises approximately 2 to 10 percent cromolyn sodium in the carrier composition, which preferably comprises a mixture of pluronic gel and lecithin organogel. The composition is prepared by mixing approximately 2 to 10 grams of cromolyn sodium powder, reduced to a fine powder by physical deformation, with approximately 5 to 7 cc of ethoxy diglycol reagent to form a semi-solid paste. A lecithin organogel syrup is prepared by dispersing approximately 100 ml of lecithin soya granular and approximately 0.9 grams of sorbic acid NF-FFC powder in approximately 117 cc of either isopropyl palmitate NF cosmetic grade or isopropyl myristate. The mixture is allowed to stand for approximately 12 hours and forms a brown liquid syrup. The syrup should be microwaved at about 850 watts for about 3 minutes to retard fungal growth. Approximately 22 to 44 cc of the lecithin organogel syrup is mixed with the cromolyn sodium paste, preferably by introducing 5 cc increments with centrifugal torque applied to the container. A pluronic gel at approximately 20 percent strength is prepared by mixing approximately 0.3 grams of potassium sodium with approximately 20 grams of pluronic F 127 NF (Poloxamer 407) and adding approximately 100 cc of purified, distilled or sterilized water. The solution is then refrigerated for at least approximately 12 hours. Physical agitation may be required to insure complete mixing. A smooth, viscous, aqueous solution is formed, which remains in the liquid state at when kept between approximately 35 to 45 degrees F. (4 to 18 degrees C.). Approximately 66 to 88 cc of the pluronic gel solution is then slowly added to the mixture of lecithin organogel and cromolyn sodium. As the mixture warms to room temperature, a smooth anoquous cream or ointment is formed.

It is understood that certain equivalents and substitutions for elements set forth above may be obvious to those skilled in the art, and the true scope and definition of the invention therefore is to be as set forth in the following claims.

What is claimed is:

1. A method for the topical treatment of vulvar vaginitis, said method comprising the topical application to the vaginal vestibule area of a therapeutically effective amount of cromolyn sodium in a carrier composition.

2. The method of claim 1, where said carrier composition comprises a mixture of pluronic gel and lecithin organogel.

3. The method of claim 2, where said pluronic gel comprises a mixture of pluronic F 127, potassium sorbate and water.

4. The method of claim 2, where said lecithin organogel comprises a mixture of lecithin, isopropyl palmitate and sorbic acid.

5. The method of claim 3, where said lecithin organogel comprises a mixture of lecithin, isopropyl palmitrate and sorbic acid.

6. The method of claim 1, where said cromolyn sodium is present in an amount between approximately 2 and 10 percent.

* * * * *